United States Patent [19]

Brode et al.

[11] Patent Number: 5,407,919
[45] Date of Patent: Apr. 18, 1995

[54] DOUBLE-SUBSTITUTED CATIONIC CELLULOSE ETHERS

[76] Inventors: George L. Brode, 653 Carlene Dr., Bridgewater, N.J. 08807; Russell L. Kreeger, 4 Cornfield Ter., Flemington, N.J. 08822; George A. Salensky, 211 Scrabbletown Rd., White House Station, N.J. 08889

[21] Appl. No.: 128,889

[22] Filed: Sep. 29, 1993

[51] Int. Cl.$^6$ .............................. A61K 31/72
[52] U.S. Cl. .................. 514/57; 424/70.1; 424/78.02; 424/78.03; 424/78.04; 424/70.13; 514/781; 514/912; 514/915; 523/105; 536/43; 536/44; 536/91
[58] Field of Search ............ 514/57, 912, 915, 781; 536/43, 44, 91; 523/105; 424/70, 78.02, 78.03, 78.04

[56] References Cited

U.S. PATENT DOCUMENTS

| | | | |
|---|---|---|---|
| 4,228,277 | 10/1980 | Landoll | 536/90 |
| 4,384,003 | 5/1983 | Kazmiroski et al. | 424/341 |
| 4,387,094 | 6/1983 | Bagros | 424/180 |
| 4,474,769 | 10/1984 | Smith | 424/180 |
| 4,551,148 | 11/1985 | Riley et al. | 604/890 |
| 4,663,159 | 5/1987 | Brode et al. | 424/70 |
| 4,707,362 | 11/1987 | Nuwayser | 424/433 |
| 4,767,463 | 8/1988 | Brode et al. | 524/27 |
| 4,845,175 | 7/1989 | Lo | 526/200 |
| 4,913,743 | 4/1990 | Brode et al. | 106/162 |
| 4,929,722 | 5/1990 | Partain et al. | 536/20 |
| 4,946,870 | 8/1990 | Partain et al. | 514/777 |

OTHER PUBLICATIONS

The Effects of Frequent Nonoxynol-9 Use on the Vaginal and Cervical Mucosa Somchai Niruthisard, MD et al., pp. 176-179 Sexually Transmitted Diseases, vol. 18, (1991).

Comparison of Vaginal Tolerance Tests of Spermicidal Preparations in Rabbits and Monkeys P. Eckstein et al., pp. 85-93, J. Reprod. Fert. (1969) vol. 20.

HEC Cellosize Hydroxyethyl Cellulose-Union Carbide Corporation, pp. 1-32, May 1991.

*Primary Examiner*—Ronald W. Griffin

[57] ABSTRACT

Double-substituted, water-soluble, cellulose ethers substituted with a cationic substituent and a hydrophobic substituent are disclosed. The levels of substitution for the cationic substituent and the hydrophobic substituent can provide enhanced properties when used in personal care compositions, such as, for example, enhanced substantivity, saline capability and low irritation potential to mucosal linings.

20 Claims, No Drawings

5,407,919

DOUBLE-SUBSTITUTED CATIONIC CELLULOSE ETHERS

FIELD OF THE INVENTION

The present invention generally relates to cellulose ethers and more specifically relates to cellulose ethers which are water-soluble and substituted with a cationic substituent and a hydrophobic substituent.

BACKGROUND OF THE INVENTION

Water-soluble cellulose ethers have been employed in a wide variety of applications, such as, for example; in personal care applications such as pharmaceutical and cosmetic compositions; and industrial applications such as viscosity adjusters, suspension aids, oil field drilling and fracturing materials and adhesion promoters.

Cationic modification of cellulose ethers is desirable particularly when the cellulose ethers are used in personal care applications, e.g., for enhanced substantivity to skin and hair. Such cationic modification is also desirable for certain industrial applications, e.g., flocculation of fines in water treatment, binders in paper manufacture, adhesion promotion to siliceous materials, etc., all of which depend on substantive properties.

Hydrophobic modification of cellulose ethers is also desirable. It provides important properties in industrial applications. For example, in latex paint, thixotropy, rheology (reversible shear dependent viscosity) and surface activity (pigment dispersion) result from hydrophobe modified cellulose ethers. However, the amount of hydrophobe that can be incorporated is restricted when water solubility is required, viz., incorporation of hydrophobe reduces water solubility.

There exists a need for new cellulose ether derivatives which display some of the above properties, but which also are saline compatible, non-irritating, substantive to mucous membranes of the eye, nose, mouth, vagina and gastrointestinal tract, and which can be formulated with therapeutic or cosmetic ingredients for personal care applications. Such new cellulose ether derivatives may also have new industrial applications as well.

SUMMARY OF THE INVENTION

In accordance with the present invention, new, double-substituted cationic, water-soluble cellulose ether derivatives are provided. The cellulose ether derivatives of the present invention are substituted with certain concentrations of a cationic substituent and a hydrophobic substituent which can provide surprisingly beneficial and unexpected properties. Quite surprisingly, it has been found that the combination of certain substitution levels of hydrophobic substituents and cationic substituents can provide synergistic effects in saline compatibility and substantivity to mucous membranes, e.g., of the eye, nose, mouth, vagina and gastrointestinal tract, in addition to being non-irritating to such mucous membranes. Moreover, the cellulose ether derivatives have other benefits as well. For example, when used in personal care compositions relating to contraception, e.g., spermicide compositions, condom lubricants, douches, and the like, the cellulose ethers of the present invention can provide sperm blocking properties. In addition, when used in ophthalmic compositions, e.g. synthetic tears, the cellulose ethers can provide excellent substantivity. Thus, the cellulose ether derivatives of the present invention are suitable for use as excipients for personal care and drug delivery compositions. Furthermore, when used in industrial applications, such as, for example; adhesion promotion to siliceous substrates, e.g., glass panels and ceramics; water-soluble coatings for plastic and metal substrates, etc.; the cellulose ethers of the present invention can provide enhanced substantivity.

DETAILED DESCRIPTION OF THE INVENTION

Cellulose ethers suitable for use in accordance with the present invention include etherified derivatives of cellulose. Typical cellulose ethers include for example, hydroxyethyl cellulose, hydroxypropyl cellulose, methyl cellulose, hydroxypropyl methyl cellulose, hydroxyethyl methyl cellulose, hydroxyethyl carboxylmethyl cellulose, and the like. Preferred cellulose ethers include hydroxyethyl cellulose and hydroxypropyl cellulose. Cellulose ethers such as described above are readily commercially available. Alternatively, such cellulose ethers can be prepared from cellulose by methods known to those skilled in the art.

The molecular weight of the cellulose ethers suitable for use in accordance with the present invention typically ranges from about 10,000 to 500,000 grams per gram mole and preferably ranges from about 20,000 to 200,000 grams per gram mole. As used herein, the term "molecular weight" means weight average molecular weight. Methods for determining weight average molecular weight of cellulose ethers are known to those skilled in the art. One preferred method for determining molecular weight is low angle laser light scattering. The viscosity of the cellulose ethers typically ranges from about 5 to 5000 centipoise, preferably from about 10 to 500 centipoise. Unless otherwise indicated, as used herein the term "viscosity" refers to the viscosity of a 2.0 weight percent aqueous solution of the polymer measured at 25° C. with a Brookfield viscometer. Such viscosity measuring techniques are known in the art.

The cellulose ether derivatives of the present invention are substituted with a first substituent and a second substituent. The first substituent is a hydrophobic substituent. The second substituent is a cationic substituent.

Hydrophobic substituents suitable for use in accordance with the present invention comprise an alkyl or arylalkyl group having about 8 to 18 carbon atoms, preferably from about 10 to 18 carbon atoms and more preferably from about 12 to 15 carbon atoms. As used herein the term "arylalkyl group" means a group containing both aromatic and aliphatic structures. Many hydrophobe-containing reagents suitable for use as hydrophobic substituents are commercially available. In addition, methods for preparing such hydrophobe-containing reagents, as well as methods for derivatizing cellulose ethers to comprise such hydrophobic substituents, are known to those skilled in the art. Note for example, U.S. Pat. No. 4,228,277 issued Oct. 14, 1980, U.S. Pat. No. 4,663,159, issued May 5, 1987 and U.S. Pat. No. 4,845,175, issued Jul. 4, 1989.

A preferred hydrophobic substituent suitable for use in accordance with the present invention has the formula:

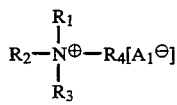

where:
- each $R_1$ and $R_2$ are $CH_3$ or $C_2H_5$;
- $R_3$ is $CH_2CHOHCH_2$ or $CH_2CH_2$;
- $R_4$ is an alkyl or arylalkyl group having about 8 to 18 carbon atoms; and
- $A_1$ is a halide ion.

Preferably, $R_1$ and more preferably, both $R_1$ and $R_2$ are $CH_3$. Preferably, $R_3$ is $CH_2CHOHCH_2$. Preferably, $R_4$ is $C_nH(2n+1)$, where n is from 8 to 18. An especially preferred hydrophobic group, i.e., $R_4$, has the formula $C_{12}H_{25}$. Chlorine is a preferred halide ion.

Other preferred hydrophobic substituents include those prepared from hydrophobe-containing reagents such as glycidyl ethers, e.g., nonylphenylglycidyl ether or dodecylphenyl glycidyl ether, or alpha-olefin expoxides, e.g., 1,2 epoxy hexadecane and their respective chlorohydrins, or alkyl halides, e.g., dodecylbromide, and mixtures thereof.

The hydrophobic substituent is typically cationic or non-ionic.

The substitution level of the hydrophobic substituents is greater than about 0.11, preferably from about greater than about 0.11 to 0.25 and more preferably from greater than about 0.11, e.g. about 0.12, to less than 0.16, e.g., about 0.15, gram moles of the hydrophobic substituent per gram mole of cellulose ether. More than one particular hydrophobic substituent can be substituted onto the cellulose ether provided that the total substitution level is within the ranges set forth above.

Preferably, the cationic substituents suitable for use in accordance with the present invention have the formula:

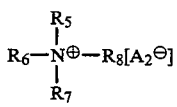

where;
- each $R_5$, $R_6$ and $R_7$ is $CH_3$ or $C_2H_5$;
- $R_8$ is $CH_2CHOHCH_2$ or $CH_2CH_2$; and
- $A_2$ is a halide ion.

Preferably, $R_5$ is $CH_3$. More preferably, $R_5$, $R_6$ and $R_7$ are $CH_3$. Preferably, $R_8$ is $CH_2CHOHCH_2$. Chlorine is a preferred halide ion. Other cationic substituents may also be used in accordance with the present invention.

Methods for preparing cationic substituents such as described above, as well as methods for derivatizing cellulose ethers to contain such cationic substituents, are known to those skilled in the art. Note for example, U.S. Pat. No. 4,663,159 issued May 5, 1987.

Preferably, the substitution level of the cationic substituent ranges from about 0.05 to 0.5 gram moles of cationic substituent per gram mole of cellulose ether. The substitution level of the cationic substituent is more preferably from about 0.05 to 0.3, and most preferably from about 0.10 to 0.25 gram moles of cationic substituent per gram mole of cellulose ether. More than one particular cationic substituent can be substituted onto the cellulose ether provided that the total substitution level is within the ranges set forth above.

The first substituent and the second substituent can be reacted onto the cellulose ether in any order. That is, the first substituent can be reacted onto the cellulose ether either prior to, subsequent to, or simultaneously with the second substituent. Preferably, the molar ratio of cation to hydrophobe is at least 1.5:1, more preferably at least 2.0:1, and most preferably at least 2.5:1. As used herein the term "molar ratio of Cation to Hydrophobe" means the total number of moles of cationic substituents per mole of hydrophobic substituent substituted on the cellulose ether. When the hydrophobic substituent is not cationic, the molar ratio of Cation to Hydrophobe is equal to the molar ratio of the second substituent to the first substituent. When the hydrophobic substituent is cationic, the molar ratio of Cation to Hydrophobe is equal to the sum of the moles of cationic substituents and hydrophobic substituents per mole of hydrophobic substituent. For example, if the substitution level of a cationic hydrophobic substituent is 0.12 gram moles per gram mole of cellulose ether, and the substitution level of the cationic substituent is 0.2 gram moles per mole of cellulose ether, then the molar ratio of Cation to Hydrophobe would be 2.67, i.e., $(0.12+0.20) \div 0.12 = 2.67$.

Preferably, the sum of the substitution levels of the first and second substituents is at least 0.18, more preferably at least 0.24 and most preferably at least 0.36 gmoles of substituents per mole of cellulose ether.

The cellulose ether derivatives of the present invention are water-soluble. As used herein, the term "water-soluble" means that at least 1 gram, and preferably at least 2 grams of the cellulose ether derivative are soluble in 100 grams of distilled water at 25° C. and 1 atmosphere. The extent of water-solubility can be varied by adjusting the extent of ether substitution on the cellulose ether and by adjusting the substitution level of the hydrophobic substituent and the cationic substituent. Techniques for varying the water solubility of cellulose ethers are known to those skilled in the art.

The cellulose ether derivatives of the present invention have a variety of end-use applications, such as, for example, industrial applications and personal care applications. Typical industrial applications include for example, use as viscosity adjusters, suspension aids, oil field drilling and fracturing materials, adhesion promotion to siliceous substrates, e.g., glass panels and ceramics, and coating materials for plastic and metal substrates. Typical personal care applications include for example, pharmaceutical and cosmetic compositions, such as, for example, contraceptive compositions, condom lubricants, vaginal ointments, douches, ophthalmic compositions, skin creams, lotions, soaps, shampoos, conditioners, and the like.

A preferred end-use application for cellulose ether derivatives of the present invention is as a component in a personal care composition which comprises the cellulose ether derivative and a personal care ingredient. As used herein, the term "personal care ingredient" includes, but is not limited to, active ingredients, such as, for example, spermicides, virucides, analgesics, anesthetics, antibiotic agents, antibacterial agents, antiseptic agents, vitamins, corticosteroids, antifungal agents, vasodilators, hormones, antihistamines, autacoids, kerolytic agents, anti-diarrhea agents, anti-alopecia agents, anti-inflammatory agents, glaucoma agents, dry-eye compositions, wound healing agents, anti-infection agents, and the like, as well as solvents, diluents and adjuvants such as, for example, water, ethyl alcohol, isopropyl alcohol, higher alcohols, glycerine, propylene glycol, sorbitol, preservatives, surfactants, menthol, eucalyptus oil, other essential oils, fragrances, viscosity adjusters and the like. Such personal care ingredients are commercially available and known to those skilled in the art.

The amount of the cellulose ether derivatives present in the personal care composition will vary depending upon the particular care composition. Typically, however, the personal care composition will comprise from about 0.1 to 99 weight percent of the cellulose ether derivative of the present invention. Typical films, such as those used in ophthalmic lenses, may contain, for example, 90 weight percent of the cellulose ether derivative.

Often, the concentration of the cellulose ether derivative in the personal care composition will range from about 0.5 to 50 weight percent, and more often from about 0.5 to 10 weight percent based on the personal care composition.

Typical spermicide compositions, e.g., foams, gels and lotions, comprise, for example, from about 1 to 5 weight percent of a spermicide such as Nonoxynol-9, from about 1 to 5 weight percent of the cellulose ether derivative of the present invention, with the balance generally comprising solvents, diluents and adjuvants such as, for example, propylene glycol, or sorbitol. Additives such as polyoxyethylene 20-sorbitan mono-laurate may also be employed in spermicide compositions in minor amounts, e.g. 1 to 5 weight percent.

Typical ophthalmic compositions, such as, for example, synthetic tears, ophthalmic lubricants, or pharmaceutical containing delivery systems, are neutrally buffered and isotonic. Levels of isotonic salts of up to about 0.9 parts by weight and up to 5 parts of the active ingredient are often included. Typical inorganic isotonic ingredients include, for example, sodium chloride, boric acid, borax, etc., while typical natural isotonic ingredients include sugars such as dextrose, mannitol and sorbitol. The pH of these solutions can vary widely from 3 to 9 and is typically from about 6 to 8. Other common ophthalmic additives include, for example, viscosity adjusters, e.g., hydroxyethyl cellulose, propylene glycols, glycerols, carbonates and bicarbonates and ethylenediaminetetraacetic acid (EDTA). A preferred additive is hyaluronic acid.

Typical personal care lubricants contain chlorohexadiene gluconate, an acidifier such as glucono-d-lactone, glycerine, one or more compounds of the present invention, preservatives such as methyl paraben, etc. Such personal care lubricants may also contain active ingredients such as, for example, spermicides, e.g., Nonoxynol-9.

Further details concerning the ingredients, amounts of ingredients and preparation methods of personal care compositions such as described above are known to those skilled in the art.

Quite surprisingly, it has been found that the combination of the above-described substitution levels of the hydrophobic and cationic substituents can provide a high degree of substantivity to mucous membranes, e.g., of the eyes, nose, mouth, vagina and gastrointestinal tract, in addition to being substantially non-irritating to such mucous membranes even in the presence of normally irritating active ingredients such as Nonoxynol-9.

Moreover, by maintaining the Cation to Hydrophobe ratio at the levels described above, i.e., preferably at least 1.5:1, more preferably 2.0:1 and most preferably at least 2.5:1, the saline compatibility of the compounds of the present invention can be enhanced. Saline compatability is an important attribute of personal care compositions. As used herein, the term "saline compatability" means that the personal care composition remains dissolved, i.e., does not separate at 25° C. and 1 atmosphere, in a saline solution, i.e., 9 grams of NaCl per liter of water, at concentrations of up to at least 2 weight percent, preferably 5 weight percent, for at least one hour, preferably at least 24 hours.

Thus, the compounds of the present invention are particularly suitable for use as excipients for personal care and drug delivery compositions, e.g., ophthalmic compositions and contraceptive compositions, because of their desirable combination of saline compatibility, low irritation potential and substantivity.

EXAMPLES

The following examples are provided for illustrative purposes and are not intended to limit the scope of the claims which follow. The following materials were used in conducting the examples.

The following ingredients were used in the Examples.

CMC—carboxymethyl cellulose having a viscosity of 400–800 centipoise, available from Aqualon Company, Wilmington, Del.

CONCEPTROL—a commercially available contraceptive composition containing CMC and POV sold by Advanced Care Products, Ortho, Johnson and Johnson, New Brunswick, N.J.

CS1—2,3 epoxypropyl trimethyl ammonium chloride available from DeGussa Corporation, sold as Quab 151.

DS—dextran sulfate having a molecular weight of 40,000–50,000 g/gmole, available from United States Biomedical Corp., Cleveland, Ohio.

HEC1—hydroxyethyl cellulose having a viscosity of 4400–6000 centipoise (1% solution) available from Union Carbide Corp., Danbury, Conn., sold as Cellosize ® QP-100M.

HPC1—hydroxypropyl cellulose having a viscosity of 1500–3000 centipoise (1% solution) available from Aqualon Company, Wilmington, Del.

HS1—3-chloro-2-hydroxypropyl dimethyldodecyl ammonium chloride available from DeGussa Corporation, Ridgefield Park, N.J., sold as Quab 342.

HS2—3-chloro-2-hydroxypropyl dimethyloctadecyl ammonium chloride available from DeGussa Corporation, Ridgefield Park, N.J., sold as Quab 426.

HS3—nonylphenylglycidyl ether available from Rhone Poulenc sold as Heloxy 64.

JR—a cationic hydroxyethyl cellulose having a viscosity of 300–500 centipoise available from Union Carbide Corp., Danbury, Conn.

N-9—Nonoxynol-9 USP available from Rhone Poulenc, Cranberry, N.J., sold as Igepal CO-630 Special.

P-20—polyoxyethylene 20-sorbitan monolaurate, available from ICI Americas, Inc., Wilmington, Del., sold as Tween 20.

P-80—polyoxyethylene 20-sorbitan mono-oleate, available from ICI Americas, Inc., Wilmington, Del., sold as Tween 80.

PG—propylene glycol USP, available from Fisher Scientific, Fairlawn, N.J.

POL. 1—a cationic, hydrophobically modified hydroxyethyl cellulose having a viscosity of 100 to 500 centipoise (2% solution) and containing a hydrophobic substituent containing a hydrocarbon portion having 12 carbon atoms and a cationic substituent, available from Union Carbide, Danbury, Conn. sold as Quatrisoft ®.

POL. 2—a cationic, hydrophobically modified hydroxyethyl cellulose having a viscosity of 50 to 500 (2% solution) centipoise and containing a hydrophobic substituent containing a hydrocarbon portion having 12 carbon atoms and a cationic substituent.

POL. 3—a cationic, hydrophobically modified hydroxyethyl cellulose having a viscosity of 50 to 500 (2% solution) centipoise and containing a hydrophobic substituent containing a hydrocarbon portion having 18 carbon atoms and a cationic substituent.

POL. 4—a non-ionic hydrophobically modified hydroxyethyl cellulose having a molecular weight of 300,000 g/gmole having a hydrophobic substituent containing a hydrocarbon portion having 16 carbon atoms available from the Aqualon Company, Wilmington, Del., sold as Natrosol ® Plus.

POL. 5—a hydrophobically modified dextran sulfate having a molecular weight of 50,000 g/gmole and containing 2.8 wt. % of a hydrophobic substituent containing a hydrocarbon portion having 15 carbon atoms.

POL. 6—a hydrophobically modified carboxymethyl cellulose having a viscosity of 50 to 500 (2% solution) centipoise and containing 1.2 wt. % of a hydrophobic substituent containing a hydrocarbon portion having 15 carbon atoms.

POV—polyvinyl pyrrolidone Povidone USP having a molecular weight of 45,000 g/gmole, available from ISP Chemicals Wayne, N.J.

SOR—sorbitol, available from Fisher Scientific, Fairlawn, N.J.

The following tests were used in the Examples.

Modified One End Test (MOET)—This test was used to determine the effect of various compounds on sperm penetration in cervical mucus. Capillary tubes containing bovine cervical mucus obtained from Serono-Baker Diagnostics Inc., Allentown, Pa. sold as Penetrax, were used to conduct the test. Each of the test compositions containing the polymer to be tested was diluted in a saline solution, i.e., at 9 grams of NaCl per liter of water, to a polymer concentration of between 0.007 w/v % and 0.45 w/v % (w/v % equals grams per 100 milliliters). The test was conducted at a concentration of either 0.003 w/v % polymer, 0.007 w/v % polymer or 1 g of test composition per 11 ml of saline. The tubes were thawed briefly and then broken open. The open end was placed in a container containing the sample in saline. The sample was allowed to migrate for 30 minutes through the tube. A semen sample was then diluted with a buffer solution to 60 million motile sperm per milliliter and mixed with the polymer sample. The tube containing the polymer sample was then re-inserted into the container containing the mixed solution and stored in an incubator at 37° C. in an atmosphere of 5 percent carbon dioxide in air for 60 minutes. The container and tube were then removed from the incubator and the tube was visually analyzed under a microscope for the migration of motile vanguard sperm through the tube. The results are expressed as percentage of migration as compared to control samples. In the control samples, the tubes were incubated with saline containing no polymer.

Double End Test (DET)—This test was also used to biologically evaluate the diffusion of the compounds in cervical mucus. The DET is similar to the MOET with the exception that the capillary tubes were exposed to the polymer samples by one end for 60 minutes and subsequently by the other end to the semen solution for 60 minutes so that sperm could migrate in the opposite direction of the polymer sample. Penetration length of vanguard motile sperm is recorded and the results are expressed as percentage of migration as compared to control samples, i.e., saline containing no polymer. The shorter sperm penetration, the greater the compounds biodiffusion. In addition, the samples used for the DET were further modified to contain 4 weight percent of N-9. The DET values reflect how far a test compound can physically diffuse in cervical mucus while still displaying sperm penetration inhibitory activity.

EXAMPLE 1

PREPARATION OF CELLULOSE ETHER DERIVATIVE

A reaction vessel equipped with a stirrer, condenser, addition funnels, and nitrogen supply, was charged with 39 grams of HEC1 and 272 grams of anhydrous acetone. The reactor was purged with nitrogen and 23 grams of an aqueous sodium hydroxide solution containing 20 wt % sodium hydroxide was added. After stirring for 30 minutes, 64 g of an aqueous solution containing 40 wt % HS1 was added. The reactor mixture was heated to 55° C. and held there for 2 hours. Then 8.7 grams of an aqueous solution containing 70 wt % CS1 was added. The mixture was held at 55° C. for another hour. The reaction was cooled and neutralized with 3 grams glacial acetic acid. The reaction slurry was filtered and washed 7 times with 400 grams of an aqueous solution containing 90 wt % acetone, once with 400 grams of an aqueous solution containing 94 wt % acetone, and once with 400 grams of a solution containing 0.5 milliliter of a 40 wt % glyoxal solution, 0.5 milliliter of acetic acid and the balance acetone. After drying, 58 grams of product containing 1.5% volatiles was obtained. The nitrogen content of the polymer was 1.60 wt. %, and the polymer had a 2% solution viscosity of 190 centipoise.

EXAMPLE 2

PREPARATION OF CELLULOSE ETHER DERIVATIVE

A reaction vessel equipped with a stirrer, condenser, addition funnels, and nitrogen supply, was charged with 39 grams of HEC1 and 272 grams anhydrous acetone. The reactor was purged with nitrogen and 16 grams of an aqueous sodium hydroxide containing 20 wt % sodium hydroxide was added. After stirring 30 minutes, 19 g of HS3 was added. The reactor mixture was heated to 55° C. and held there for 2 hours. Then 8.7 grams of an aqueous solution containing 70 wt % CS1 was added. The mixture was held at 55° C. for another hour. The reaction was cooled and neutralized with 3 grams glacial acetic acid. The reaction slurry was filtered and washed 7 times with 400 grams of an aqueous solution containing 90 wt % acetone, once with 400 grams of an aqueous solution containing 94 wt % acetone, and once with 400 grams of a solution containing 0.5 milliliter of a 40 wt % glyoxal solution, 0.5 milliliter of acetic acid and the balance acetone. After drying, about 60 grams of product containing 5 wt % volatiles was obtained.

The nitrogen content of the polymer was 1.20 wt. %, and the polymer had a 2% solution viscosity of 200 centipoise.

CONTROL EXAMPLE 3

PREPARATION OF DEXTRAN SULFATE DERIVATIVE

Approximately 41.36 grams of t-butyl alcohol 2.64 grams of water and 0.47 grams of sodium chloride were added to a 3-neck round bottom 250 milliliter flask fitted with a stirrer, a reflux condenser and a nitrogen inlet with a septum. The ingredients were mixed until thoroughly dissolved and 6.2 grams of DS were added. The flask was purged with nitrogen for one hour. Then 0.3 milliliter of an aqueous solution containing 45 wt. % potassium hydroxide was added dropwise with a syringe through the septum and mixed for one hour. Approximately 4.1 grams of HS3 mixed with 4.1 grams of t-butyl alcohol was then added to the flask with the syringe, mixed for one half hour and then heated to reflux conditions for 8 hours. Then the flask was cooled and 3 drops of glacial acetic acid were added. Thereafter, about 150 milliliters of acetone were added and mixed for 15 minutes. The solids were recovered by filtration, then about 150 milliliters of acetone were added to the solids and mixed for 15 minutes and filtered. This washing and filtering process was repeated 3 times, after which the solids were dried in a 50° C. oven under vacuum conditions. The resulting polymer was found to have 2.5 wt. % nonylphenylglycidyl ether as measured by ultraviolet spectroscopy.

CONTROL EXAMPLE 4

PREPARATION OF CELLULOSE ETHER DERIVATIVE

Approximately 115 grams of t-butyl alcohol and 15.0 grams of water were added to a 3-neck flat bottom flask such as described in Example 3. The ingredients were mixed until dissolved and 22.0 grams of sodium carboxymethyl cellulose were added. The flask was purged with nitrogen for 1 hour. Approximately 3.9 milliliters of an aqueous solution containing 50 wt. % sodium hydroxide was added dropwise with a syringe through the septum and mixed for 1 hour. Then 3.0 grams of HS3 mixed with 6.0 grams of t-butyl alcohol was added. The ingredients were mixed for one-half hour and then heated to reflux for 7 hours. The flask was cooled and 12 grams of glacial acetic acid were added. Then approximately 150 milliliters of an aqueous solution containing 90 wt. percent acetone were added and mixed for 15 minutes. The solids were recovered by filtration. The solids were then washed with acetone and filtered 3 times. The product was dried in a 50° C. oven under vacuum conditions. The polymer was found to have 1.2 wt. % nonylphenylglycidyl ether as measured by ultraviolet spectroscopy.

EXAMPLE 5

PREPARATION OF CONTRACEPTIVE COMPOSITIONS

Several cellulose ether derivatives were prepared in accordance with the procedure set forth in Examples above. The cellulose ether derivatives were then formulated into contraceptive compositions suitable for evaluation purposes. The compositions were formulated to contain either 1.25 or 2.5 weight percent of the cellulose ether, 0, 1.25 or 2.5 weight percent of P-20 or P-80 with the balance comprising water. The levels of Substituent 1 and Substituent 2, as well as the amount of cellulose ether in the samples are set forth in Table 1 below. In addition, MOET and DET values are also set forth in Table 1. For the DET, the compositions were further modified to contain 4 wt. % N-9.

TABLE 1

CONTRACEPTIVE COMPOSITIONS

| SAMPLE | POLYMER | AMOUNT OF CELLULOSE ETHER WT % | SUBSTITUENT 1 TYPE | SUBSTITUENT 1 AMOUNT mol/mol | SUBSTITUENT 2 TYPE | SUBSTITUENT 2 AMOUNT mol/mole | MOET (0.007 w/v %) | MOET (1 g test composition per (11 ml) | DET |
|---|---|---|---|---|---|---|---|---|---|
| 1 | POL. 1 (control) | 1.25 | HS1 | 0.08 | CS1 | | 50 | | 71 |
| 2 | POL. 2 | 1.25 | HS1 | 0.12 | CS1 | 0.23 | 12 | 0 | 60 |
| 3 | POL. 2 | 1.25 | HS1 | 0.16 | CS1 | 0.08 | 64 | | 61 |
| 4 | POL. 3 (control) | 2.5 | HS2 | 0.04 | CS1 | 0.06 | 53* | | 75 |
| 5 | POL. 2 (control) | 1.25 | HS1 | 0.06 | CS1 | 0.10 | 7 | | 71 |
| 6 | HEC 1 (control) | 3.0 | | | | | | 100 | |
| 7 | JR (control) | 6.0 | | | CS1 | 0.40 | | 89 | |
| 8 | POL. 4 (control) | 3.0 | | | | | | 77 | |
| 9 | CMC/POV (control) | 2.5 | | | | | 95 | 97 | 84 |
| 10 | POL. 5 (control) | 1.25 | HS3 | | | | | 40 | |
| 11 | POL. 6 (control) | 1.25 | HS3 | | | | | 22 | |

*Tested at 0.003 w/v %
NOTES:
1. Samples 1, 2, 3, 5, 10 and 11 contained 1.25 wt. % P-20
2. Sample 4 contained 2.5 wt. % P-80
3. Samples 6, 7, 8 and 9 did not contain P-20 or P-80.

The data in Table 1 demonstrate that, quite surprisingly, only the cationic, hydrophobically modified cellulose ethers, i.e., Pol. 1 (Control), Pol. 2 and Pol. 3, provided significant sperm blocking properties, i.e., MOET values less than 65 at a concentration of 0.007 w/v %. In contrast, Pol. 4 (Control), which is hydrophobically modified and nonionic, provided a MOET value of 77 as compared to POL. 2 which had an MOET value of 0 at a test composition concentration of 1 g/11 milliliters. Unmodified HEC1 provided a MOET value of 100% at a test composition concentration of 1 g/11 milliliters. A cationic cellulose ether, i.e., JR (Control), which was not hydrophobically modified, provided a MOET of 89% at a test composition concentration of 1 g/11 milliliters. Two hydrophobically modified anionic polysaccharides, i.e., POL. 5 (Control) and POL. 6 (Control), provided MOET values of 40% and 22% respectively at a test composition concentration of 1 gram per 11 milliliters as compared to the cationic hydrophobically modified polysaccharides, e.g., POL. 2, which had a MOET value of 0% at the same concentration. In addition, the data in Table 1 also demonstrate, quite surprisingly, that at substitution levels for the hydrophobic substituent of less that 0.12, sperm penetration as evidenced by the DET values, significantly increased, i.e. greater than about 65% e.g., Samples 1, 4 and 5. Accordingly, collectively, the above described data from the MOET and DET demonstrate that the double-substituted, cationic, hydrophobically modified cellulose ether derivatives of the present invention having a substitution level of the hydrophobic substituent of at least greater than 0.11 provided unexpectedly enhanced performance with respect to reducing sperm motility.

EXAMPLE 6
SPERM PENETRATION INHIBITION

A MOET was run comparing the sperm blocking effect of a hydrophobically modified polysaccharide, i.e., POL 2, and a saline modifier, i.e., P-20. At a polymer concentration of 0.003 w/v %, the MOET value for POL 2 was 19% and the MOET value for P-20 was 96%. These results clearly demonstrate that the sperm penetration inhibitory activity observed is intrinsic to the hydrophobically modified polysaccharide itself.

EXAMPLE 7
PREPARATION OF OPHTHALMIC COMPOSITIONS

The cationic hydrophobically modified cellulose ethers of the present invention were combined with various common ingredients in order to prepare a synthetic tear solution, an isotonic ophthalmic solution an ophthalmic lubricant and ophthalmic lubricant with an active i.e., 1 wt. % tetraethylammonium chloride. Table 2 below sets forth the detailed compositions.

TABLE 2
OPHTHALMIC COMPOSITIONS

| INGREDIENT | SYNTHETIC TEARS WT % | ISOTONIC SOLUTION WT % | LUBRICANT WT % | LUBRICANT AND ACTIVE WT % |
|---|---|---|---|---|
| POL. 2 | 0.10 | 0.10 | 0.10 | 0.10 |
| WATER | 98.745 | 97.15 | 98.9 | 97.9 |
| Hydroxyethyl cellulose | 0.15 | | | |
| Sodium Chloride | | 0.80 | 0.80 | 0.80 |
| Sodium Bicarbonate | | 0.10 | 0.10 | 0.10 |
| Disodium EDTA | | 0.10 | 0.10 | 0.10 |
| Benzoalkonium chloride | 0.005 | | | |
| Glycerol | | 2.75 | | |
| Tetraethyl-ammonium chloride | | | | 1.00 |
| | 100.000 | 100.000 | 100.000 | 100.000 |

EXAMPLE 8
SUBSTANTIVITY

Approximately 100 grams of POL. 2 was dissolved in water to form a 2.5 wt. % solution. The solution was then applied to 2 regions of a negatively charged vinyl substrate which is often used to simulate skin. A 2 wt % sodium fluorescein ophthalmic dye was applied to one of the coated areas and to an uncoated area. The fluorescein dye was then washed off with a 0.9 wt. % sodium chloride solution and the three areas were examined with ultraviolet light having a wave length of 365 nanometers.

The area coated with POL. 2 and exposed to the fluorescein dye was very fluorescent, whereas the area which was not coated with POL. 2 and exposed to the fluorescein showed almost no fluorescence. The area coated with POL. 2 but not treated with the dye also showed almost no fluorescence. Thus, the cationic hydrophobically modified cellulose ethers of the present invention can provide enhanced substantivity of substrates.

Those skilled in the art will recognize that although the present invention has been described with respect to specific aspects, other aspects are intended to be included within the scope of the claims which follow. For example, cellulose ethers other than those specifically described herein can be used in place of the cellulose ethers described herein. In addition, alternative cationic substituents and hydrophobic substituents can be used other than those specifically described herein. Similarly, the cellulose ether derivatives of the present invention can, of course, be used in other end-use applications than those specifically described herein.

We claim:

1. A double-substituted, cationic, water-soluble cellulose ether comprising;
   (a) from greater than about 0.11 to about 0.25 gram mole per gram mole of cellulose ether of a first substituent having the formula;

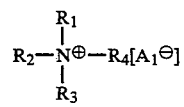

where;

each $R_1$ and $R_2$ are $CH_3$ or $C_2H_5$;
$R_3$ is $CH_2CHOHCH_2$ or $CH_2CH_2$
$R_4$ is an alkyl or arylalkyl group having about 8 to 18 carbon atoms; and
$A_1$ is a halide anion; and
   (b) from about 0.05 to 0.50 gram moles per gram mole of cellulose ether of a second substituent having the formula;

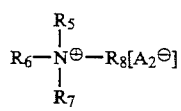

where;

each $R_5$, $R_6$ and $R_7$ is $CH_3$ or $C_2H_5$;

$R_8$ is $CH_2CHOHCH_2$ or $CH_2CH_2$; and $A_2$ is a halide anion;

wherein the molar ratio of Cation to Hydrophobe is at least 1.5 to 1.

2. The compound of claim 1 wherein $R_4$ has from about 10 to 18 carbon atoms.

3. The compound of claim 2 wherein $R_4$ is an alkyl group having the formula, $C_{12}H_{25}$.

4. The compound of claim 1 which comprises from about 0.10 to 0.25 gram mole of the second substituent per mole of cellulose ether.

5. The compound of claim 1 wherein the molar ratio of Cation to Hydrophobe is at least 2.0.

6. The compound of claim 1 wherein the cellulose ether is selected from the group consisting of hydroxyethyl cellulose and hydroxypropyl cellulose.

7. A double-substituted, cationic, water-soluble cellulose ether comprising:

(a) from less than about 0.11 to about 0.25 gram mole per gram mole of cellulose ether of a first substituent selected from the group consisting of glycidylethers, alpha-olefin epoxides, alkylhalides and mixtures thereof having an alkyl or arylalkyl group with from about 8 to 18 carbon atoms; and (b) from about 0.05 to 0.50 gram moles per gram mole of cellulose ether of a second substituent having the formula;

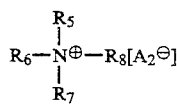

where;

each $R_5$, $R_6$ and $R_7$ is $CH_3$ or $C_2H_5$;

$R_8$ is $CH_2CHOHCH_2$ or $CH_2CH_2$; and $A_2$ is a halide anion;

wherein the molar ratio of Cation to Hydrophobe is at least 1.5 to 1.

8. The compound of claim 7 wherein the first substituent is selected from the group consisting of nonylphenylglycidyl ether, dodecylphenylglycidyl ether, 1,2 epoxy hexadecane, and dodecylbromide.

9. The compound of claim 7 wherein the first substituent has an alkyl or arylalkyl group with from about 10 to 18 carbon atoms.

10. The compound of claim 7 which comprises from about 0.10 to 0.25 gram mole of the second substituent per mole of cellulose ether.

11. The compound of claim 7 wherein the molar ratio of Cation to Hydrophobe is at least 2.0.

12. The compound of claim 7 wherein the cellulose ether is selected from the group consisting of hydroxyethyl cellulose and hydroxypropyl cellulose.

13. A personal care composition comprising at least one personal care ingredient and the compound of claim 1.

14. A personal care lubricant composition of claim 13 wherein the personal care ingredient comprises chlorohexadiene gluconate, glucono-d-lactone, and glycerine.

15. A personal care ophthalmic composition of claim 13 wherein the personal care ingredient comprises water and an isotonic ingredient.

16. A synthetic tear ophthalmic composition of claim 15 wherein the personal care ingredient comprises water, an isotonic ingredient, and a viscosity adjuster.

17. A personal care composition comprising at least one personal care ingredient and the compound of claim 7.

18. A personal care lubricant composition of claim 17 wherein the personal care ingredient comprises chlorohexadiene gluconate, glucono-d-lactone, and glycerine.

19. A personal care ophthalmic composition of claim 17 wherein the personal care ingredient comprises water and an isotonic ingredient.

20. A synthetic tear ophthalmic composition of claim 19 wherein the personal care ingredient comprises water, an isotonic ingredient, and a viscosity adjuster.

* * * * *